Figure 1:
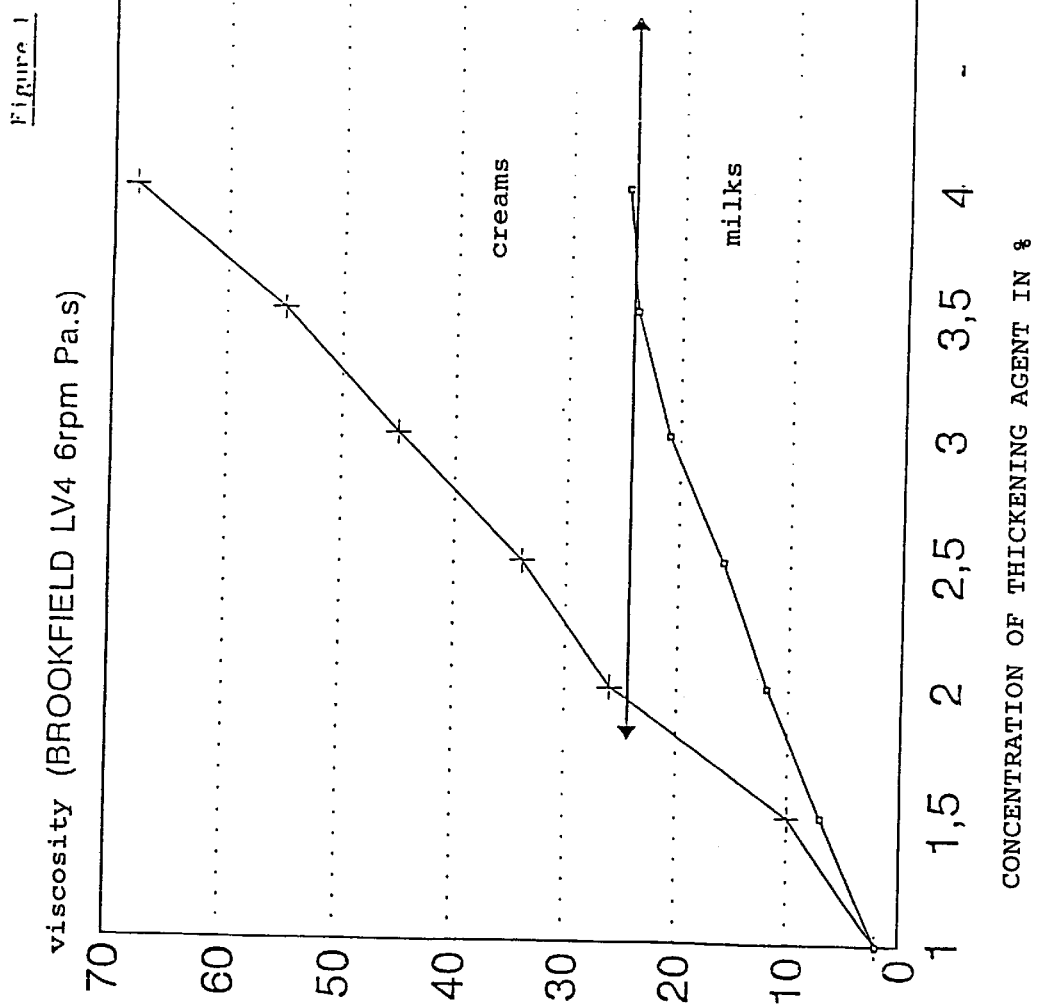

United States Patent

Michel-Lecocu et al.

[11] Patent Number: 6,136,305
[45] Date of Patent: Oct. 24, 2000

[54] TOPICAL COMPOSITION COMPRISING A THICKENER OF ACRYLIC ACID-ACRYLAMIDE WATER-IN-OIL EMULSION

[75] Inventors: Nelly Michel-Lecocu, Maisons-Alfort; Chantal Amalric, Blan, both of France

[73] Assignee: Societe d'Exploitation de Produits pour les Industries Chimiques, S.E.P.P.I.C., Paris, France

[21] Appl. No.: 08/904,931

[22] Filed: Aug. 1, 1997

Related U.S. Application Data

[63] Continuation of application No. 08/596,186, filed as application No. PCT/FR95/00833, Jun. 22, 1995, abandoned.

[30] Foreign Application Priority Data

Jun. 22, 1994 [FR] France ................................. 94 07636

[51] Int. Cl.$^7$ ............................ A61K 7/48; A61K 31/78; C08J 3/05
[52] U.S. Cl. .................. 424/78.03; 424/401; 523/337
[58] Field of Search ........................ 424/78.03, 401; 523/337

[56] References Cited

U.S. PATENT DOCUMENTS

| | | | |
|---|---|---|---|
| 3,997,492 | 12/1976 | Kane et al. | 524/801 |
| 4,335,103 | 6/1982 | Barker et al. | 424/59 |
| 4,379,883 | 4/1983 | Zecher | 524/801 |
| 4,525,581 | 6/1985 | Denzinger et al. | 528/503 |
| 4,585,820 | 4/1986 | Defago et al. | 524/308 |
| 5,073,371 | 12/1991 | Turner et al. | 424/401 |
| 5,162,474 | 11/1992 | Bresciani | 526/306 |
| 5,288,493 | 2/1994 | Martino et al. | 424/401 |
| 5,324,765 | 6/1994 | Mondet et al. | 524/555 |
| 5,516,508 | 5/1996 | Thaman et al. | 424/59 |
| 5,520,905 | 5/1996 | Uhlmann et al. | 424/59 |

FOREIGN PATENT DOCUMENTS

| | | |
|---|---|---|
| 0 186 361 | 7/1986 | European Pat. Off. . |
| 0 424 260 | 4/1991 | European Pat. Off. . |
| 0 494 022 | 7/1992 | European Pat. Off. . |
| 3730781 | 3/1989 | Germany . |
| 5-302075 | 11/1993 | Japan . |
| WO 92/21316 | 12/1992 | WIPO . |

OTHER PUBLICATIONS

The Condensed Chemical Dictionary, Eighth Edition, Van Nostrand Reinhold Company, New York, New York, 1971, p. 657.
Hackh's Chemical Dictionary, Fourth Edition, McGraw–Hill Book Company, New York, New York, 1969, p. 488.

*Primary Examiner*—Robert E. Sellers
*Attorney, Agent, or Firm*—Young & Thompson

[57] ABSTRACT

A thickener comprises a water-in-oil reverse emulsion and a copolymer having moieties derived (i) from a monounsaturated monocarboxylic acid monomer containing from 3 to 5 carbon atoms, the monocarboxylic acid either being in free form or in the form of an inorganic salt, and (ii) from a monoacrylamide monomer. The copolymer is in solution in the aqueous phase constituting the emulsion, the oil phase of this emulsion consisting of a mixture of at least one volatile oil and at least one non-volatile oil. The weight ratio between the volatile oil and the non-volatile oil is between 90/10 and 10/90. The oil phase represents from 10 to 60% by weight of the whole. Water represents from 30 to 70% by weight of the whole. The copolymer represents from 10 to 30% by weight of the whole and a surfactant represents from 5 to 20% by weight of the whole.

4 Claims, 1 Drawing Sheet

TOPICAL COMPOSITION COMPRISING A THICKENER OF ACRYLIC ACID-ACRYLAMIDE WATER-IN-OIL EMULSION

This application is a continuation of application Ser. No. 08/596,186 filed Feb. 15, 1996, now abandoned, which was the 35 USC 371 national phase of International application PCT/FR95/00833, filed on Jun. 22, 1995, which designated the United. States.

The present invention relates, on the one hand, to a topical composition, which is useful in particular in cosmetics and in dermopharmacy, comprising an aqueous phase and a thickener, and, on the other hand, to a novel thickener in its normal state, which is well tolerated by the skin and mucosae.

Patent application EP-A-0,424,260 and international application WO 92/21316 describe cosmetic compositions or compositions for treating keratinous material which may comprise an ammonium acrylate/acrylamide copolymer dispersed in a water-in-oil emulsion. This dispersion comprises oleosoluble surfactants having a hydrophilic/lipophilic balance (or HLB) of less than 7. It is useful as a thickener. The Applicant has, however, been able to observe that this type of thickener, in the form of a dispersion, is poorly suited to the preparation of certain compositions, such as emulsions comprising at least one oil phase and at least one aqueous phase. The reason for this is that this type of thickener is difficult to mix with the polar oils liable to constitute the oil phase of these emulsions.

Patent application EP-A-0,503,853 describes topical compositions, that is to say compositions intended to be applied to human or animal skin or mucosae, comprising a thickener consisting of a water-in-oil reverse emulsion and a copolymer. The copolymer is essentially in solution in the aqueous phase constituting the said reverse emulsion. The copolymer consists of units derived (a) from a monoacrylamide monomer, (b) from a 2-acrylamido-2-methylpropanesulphonic (AMPS) acid monomer and (c) from a polyfunctional monomer. Such a thickener has the advantage of being able to invert itself when it is diluted in a hydrophilic phase. Thus, when the thickener which comprises a water-in-oil reverse emulsion is mixed with the other components forming the said topical composition, the sense of the emulsion is reversed, such that the aqueous phase becomes continuous. This thickener is entirely suitable for the preparation of topical compositions comprising, in particular, polar oils with which it is fully miscible. The thickener also has the advantage of being relatively well tolerated by the skin tissues and mucosae on which it is applied.

However, the Applicant has been able to observe that the thickeners used in the topical compositions according to patent application EP-A-0,503,853 could not conveniently be used for the manufacture of all types of topical compositions. Thus, it may be difficult to prepare fluid emulsions, thickened by thickeners of this type, in a reproducible manner in terms of viscosity. "Fluid emulsions" is understood here to refer to topical compositions having a viscosity of less than about 25 Pa s (Brookfield, LV4, 6 revolutions/minute). The reason for this is that topical compositions of this type require relatively low contents of the said thickener. Now, on account of the nature of the latter, slight variations in the thickener concentrations used may lead to considerable variations in the viscosity of the topical composition. It is thus difficult to prepare topical compositions with such a thickener in a reproducible manner on an industrial scale.

It has also been observed that the viscosity-modifying effect afforded by the thickener described in the above document is reduced when this thickener is combined in the topical composition with electrolytes, such as sodium chloride or magnesium chloride.

Moreover, patent application EP-A-0,186,361 describes thickeners which are useful for preparing pasty printing inks. The thickener consists in particular of a water-in-oil emulsion comprising an aqueous phase in which is dissolved a homopolymer or copolymer based, preferably, on moieties derived from acrylic acid. Like the thickener described in EP-A-0,503,853, this thickener is prepared according to the process, which is known per se, of reverse emulsion polymerization. According to this process, the polymerization of monomers is performed in a water-in-oil emulsion. The oil phase constituting this emulsion is usually based on a volatile oil, such as an isoparaffin oil. However, the Applicant has observed that this thickener was not well tolerated by the skin.

The Applicant has thus developed a topical composition which constitutes a first subject of the invention, circumventing the abovementioned drawbacks of topical compositions. More particularly, the topical composition according to the invention comprises a thickener based on a reverse emulsion, which is well tolerated by the tissues on which it is applied, and which moreover has a viscosity which is stable even in the presence of electrolytes.

According to another aspect, the invention relates to topical compositions, in particular fluid emulsions, comprising a thickener, it being possible for the said topical composition to be readily prepared in a reproducible manner on an industrial scale.

According to yet another aspect, the invention relates to a thickener comprising a copolymer, which may readily be used for thickening and emulsifying a topical composition comprising a reverse emulsion, the said thickener making it possible to obtain very good tolerance with respect to the tissues on which it is applied.

The present invention thus relates to a topical composition comprising at least one aqueous phase, a non-volatile oil and a thickener, characterized in that the thickener is chosen from those comprising a water-in-oil reverse emulsion and a copolymer having moieties derived (i) from a monounsaturated monocarboxylic acid monomer containing from three to five carbon atoms, the monocarboxylic acid either being in free form or in the form of an inorganic salt, and (ii) from a monoacrylamide monomer, the copolymer being in solution in the aqueous phase constituting the reverse emulsion and the oil phase of the reverse emulsion comprising at least one volatile oil.

Within the context of the present invention, it is clearly understood that the sense of the emulsion constituting the thickener is the sense existing prior to the mixing of this thickener with the other components constituting the topical composition, in particular the hydrophilic components. Thus, it is notable that the thickener, in accordance with the invention, comprising a water-in-oil reverse emulsion, may invert to form an emulsion in which the continuous phase is an aqueous phase, this inversion taking place during dilution of the thickener with a hydrophilic phase constituting the topical composition.

After inversion, the copolymer is released into the continuous phase and thereby imparts increased viscosity thereto.

Other aspects of the present invention will emerge from the description which follows and from the FIG. 1.

The FIG. 1 represents the viscosity, measured by a Brookfield LV4 viscometer rotating at 6 revolutions/minute, of a topical composition obtained using increasing concentrations of a thickener in accordance with the invention, compared with the viscosity of a similar topical composition of the prior art, also comprising a thickener.

The Applicant has observed that a topical composition comprising a non-volatile oil as well as a thickener as described above was perfectly tolerated by the tissues on which it was applied.

The non-volatile oil present in the topical composition may be a constituent, at least in part, of the oil phase of the reverse emulsion forming the thickener. This oil phase thus consists essentially of a mixture of at least one volatile oil and at least one non-volatile oil. In this case, the weight ratio between the volatile oil and the non-volatile oil in the water-in-oil reverse emulsion forming the thickener is usually between 90/10 and 10/90, preferably between 30/70 and 70/30.

The weight ratio between the non-volatile oil and the volatile oil in the topical composition in accordance with the invention is usually greater than 0.5:1, preferably greater than 0.9:1 and more generally between 1:1 and 100:1.

Within the context of the present invention, in order to determine whether or not an oil is volatile, the following test is performed: 3 g of the oil to be considered are introduced into a 250 ml container which is maintained at 220° C. for 1 h 30. The weight loss is then measured. An oil is considered as being volatile if, under these conditions, the percentage weight loss is greater than 5%.

As volatile oils which are suitable within the context of the invention, mention may be made of volatile isoparaffins and volatile silicone oils, in particular volatile cyclomethicones. The volatile isoparaffins which may be used in the context of the present invention have a saturated branched hydrocarbon structure and a molecular weight of less than about 200. Isoparaffin oils which may more particularly be mentioned are ISOPAR M and ISOPAR L marketed by the company Exxon.

Non-volatile oils which may be mentioned are thickened or light liquid paraffins as defined in the European Pharmacopoeia, triglycerides of plant origin (plant oil), esters formed by condensation between a fatty acid and a monoalcohol, the said ester containing more than 10 carbon atoms, preferably from 14 to 34 carbon atoms, such as cetearyl octanoate or isostearyl isostearate, and non-volatile silicone oils such as non-volatile dimethicones.

According to an advantageous aspect of the invention, the volatile oil is an isoparaffin oil and the non-volatile oil comprises at least one liquid paraffin or isostearyl isostearate.

The monounsaturated monocarboxylic acid constituting the said copolymer may be chosen from the group consisting of acrylic acid, methacrylic acid, methylmethacrylic acid or mixtures of these acids, these acids being in free form or in the form of an inorganic salt. When these acids are in the form of a salt, this is advantageously a salt of an alkali metal, preferably sodium, or even an ammonium salt. Acrylic acid in free form or in sodium salt form is preferred within the context of the present invention.

The molar ratio between the monocarboxylic acid and the acrylamide constituting the said copolymer may be between 85/15 and 15/85, preferably between 60/40 and 40/60.

The copolymer also usually contains a polyfunctional monomer. This monomer may consist of methylenebis(acrylamide) (MBA), diallyl phthalate, glycol diacrylates, triallyl cyanurate, triallyl isocyanurate, polyfunctional alkylene-ethers, allyl methacrylate or mixtures of one or more of these polyfunctional monomers. A polyfunctional monomer preferred within the context of the present invention consists of MBA.

The content of polyfunctional monomers present in the copolymer may be between 0.1 and 2 milliequivalents/mol of the other monomers.

The thickener may also advantageously contain one or more surfactants. These surfactants are preferably of the nonionic type, such as polyethoxylated fatty alcohols, polyethoxylated alkylphenols such as polyethoxylated nonylphenol, polyethoxylated sorbitan esters, sorbitan esters, alkylolamides or alkyl polyglycosides, in particular those defined in patent applications EP-A-0,077,167 or EP-A-0,358,216, reference to which is incorporated in the present description.

According to a most particularly advantageous aspect of the present invention, the thickener used comprises one or more surfactants whose HLB is greater than or equal to 8, preferably greater than or equal to 10.

A thickener according to the invention may be prepared according to the process described in patent application EP-A-0,186,361, reference to which is incorporated in the present description, in particular the passages on page 7, lines 1–9 and page 10, lines 22–37, as well as Examples 1, 3 and 5.

According to that process, the various monomers constituting the copolymer are placed in aqueous solution. This aqueous solution is then mixed with an oil phase comprising one or more surfactants, in particular nonionic surfactants. These surfactants have an HLB value of less than 9. The aqueous solution and the oil phase thus form a water-in-oil emulsion, after which the monomers of the aqueous phase are copolymerized using, in a conventional manner, polyfunctional monomers such as those mentioned above.

The oil constituting the oil phase of the said water-in-oil reverse emulsion usually consists of one or more volatile oils.

When the thickener in accordance with the invention contains a non-volatile oil, this oil may be incorporated into the oil phase of the water-in-oil emulsion after copolymerization. Nonionic surfactants such as those mentioned above may also be added after copolymerization, for the purpose of obtaining an HLB greater than or equal to 8 preferably greater than or equal to 10.

According to an advantageous aspect of the present invention, the thickener used comprises a water-in-oil emulsion containing from 10 to 60% by weight of oil phase, from 30 to 70% by weight of water, from 10 to 30% by weight of a copolymer and from 5 to 20% by weight of surfactant.

A topical composition according to the invention, intended to be applied to human or animal skin or mucosae, may consist of a topical emulsion comprising at least one aqueous phase and at least one oil phase. This topical emulsion may be of the oil-in-water type. More particularly, this topical emulsion may consist of a fluid emulsion, such as a milk or a fluid gel. The oil phase of the topical emulsion may consist of a mixture of one or more oils.

A topical composition according to the invention may be intended for a cosmetic use or may be used in order to prepare a medicinal product intended for the treatment of skin diseases and mucosal diseases. In the latter case, the topical composition then contains an active principle which may consist, for example, of an anti-inflammatory agent, a muscle relaxant, an antifungal agent or an antibacterial agent.

When the topical composition is used as a cosmetic composition intended to be applied to the skin or the mucosae, it may or may not contain an active principle, for example a moisturizing agent, a tanning agent, a sunscreen, an anti-wrinkle agent, an agent intended for slimming, an anti-free-radical agent, an antiacne agent or an antifungal agent.

A topical composition according to the invention usually contains between 0.1 and 10% by weight of the thickener defined above. The pH of the topical composition is preferably above or equal to 5, and is more preferably between 6 and 12.

The topical composition may also contain compounds conventionally included in compositions of this type, for example fragrances, preserving agents, dyes, emollients or surfactants.

A topical composition according to the invention may be prepared in a manner known to those skilled in the art, for example according to the process described in patent application EP-A-0,503,853.

According to another aspect, the invention relates to a novel thickener comprising a water-in-oil emulsion and a copolymer, the copolymer having moieties derived (i) from a monounsaturated monocarboxylic acid containing from three to five carbon atoms, the monocarboxylic acid being in free form or in the form of an inorganic salt, and (ii) from a monoacrylamide monomer, the copolymer being in solution in the aqueous phase constituting the said emulsion, the oil phase of the said emulsion consisting of a mixture between at least one volatile oil and at least one non-volatile oil.

The various quantitative and qualitative characteristics of this thickener are as described above.

According to a most particularly advantageous aspect of the invention, the said oil phase constituting the thickener in accordance with the invention comprises a mixture between, on the one hand, an isoparaffin oil and, on the other hand, a liquid paraffin or isostearyl isostearate.

According to yet another aspect, the invention relates to the use of the novel thickener in accordance with the invention mentioned above, for thickening and emulsifying a topical composition comprising at least one aqueous phase.

The examples which follow are intended to illustrate the present invention.

EXAMPLE 1

A thickener in accordance with the present invention is prepared using the process described in patent application EP-A-0,186,361, so as to obtain a water-in-oil emulsion having the following composition (% by weight):

| copolymer comprising: | |
| --- | --- |
| moieties derived from a monoacrylamide monomer | 7.5% |
| moieties derived from a sodium acrylate monomer | 9.5% |
| N,N-methylenebis(acrylamide) | 0.2 meq/mol of monomer |
| isoparaffin | 15% |
| liquid paraffin | 15% |
| montanox 95 SPI[1] | 4% |
| laureth 7[2] | 2% |
| water qs | 100% |

[1]polysorbate marketed by the company Seppic
[2]lauryl alcohol ethoxylated with 7 units of ethylene oxide.

Copolymerization of the monomers is performed according to the reverse emulsion polymerization process, in a water-in-oil emulsion whose oil phase consists of isoparaffin. The liquid paraffin is introduced into the mixture obtained after copolymerization.

EXAMPLE 2

Another thickener in accordance with the present invention is prepared according to the process described in patent application EP-A-0,186,361. To this end, in a first stage, a water-in-oil emulsion is prepared, comprising:

| copolymer comprising moieties derived: | |
| --- | --- |
| from a monoacrylamide monomer | 8.3% |
| from a sodium acrylate monomer | 10.8% |
| N,N-methylenebis(acrylamide) | 0.2 meq/mol of monomer |
| isoparaffin | 15% |
| montane 80[3] | 1.2% |
| oleamide DEA[4] | 2.4% |
| water | 38.3% |

[3]sorbitan oleate marketed by the company Seppic
[4]mixture based on oleic acid diethanolamide (INCI nomenclature)

and, in a second step, a mixture comprising 15% by weight of isostearyl isostearate and 9% by weight of montanox 60[5] (relative to the total weight of the final emulsion obtained) is then introduced into this emulsion.

(5): sorbitan stearate ethoxylated with 20 units of ethylene oxide (or Polysorbate 60), marketed by the company Seppic.

EXAMPLE 3

The process is performed as in Example 1, using 12% by weight of monoacrylamide monomer and 6% by weight of a sodium acrylate monomer, so as to obtain another thickener in accordance with the invention.

EXAMPLE 4

An oil-in-water emulsion is prepared by mixing the following compounds (% by weight):

| thickener | x % |
| --- | --- |
| primol 352[6] | 10% |
| water qs | 100% |

[6]liquid paraffin marketed by the company Esso.

The thickener used is either that of Example 1, in accordance with the invention, or a thickener comprising the copolymer as prepared in Example 1 of patent application EP-A-0,503,853, by way of comparison. The comparative thickener is prepared according to the process of Example 1 of EP-A-0,503,853, after adaptation for the purpose of obtaining a composition which differs from that of the thickener in accordance with the invention only in the actual nature of the copolymer. This adaptation consists in diluting the thickener according to Example 1 of EP-A-0,503,853 with water and suitable oils, in order for the concentration of copolymers to be identical to that of the copolymer of the thickener according to Example 1 above.

The oil phase, the aqueous phase and the various surfactants are thus quantitatively and qualitatively identical for each thickener tested. Furthermore, each of these thickeners contains an identical concentration of copolymers.

Measurement is made of the viscosity of various oil-in-water emulsions as defined above, comprising variable concentrations of thickener in accordance with the invention or of thickener according to the prior art.

The viscosity measured is expressed in Pa s. It is measured using a Brookfield LV4 viscometer rotating at 6 revolutions/minute. The results obtained are presented in FIG. 1. The viscosity is on the y-axis. The concentration of thickener (% by weight) is on the x-axis.

It is considered that below a viscosity of about 25 Pa s, the oil-in-water emulsion is a milk (fluid emulsion) and that above this value, it is in the form of a cream.

It may be observed that as soon as the concentration of thickener according to the prior art exceeds 2% by weight, the said emulsion is in the form of a cream. In contrast, the thickener in accordance with the invention may be used at concentrations of greater than 3% by weight without the emulsion being in the form of a cream.

The figure also shows that the curve in accordance with the invention has a much lower slope than that obtained with a thickener according to the prior art. It emerges therefrom that slight variations in concentration of the thickener according to the invention do not significantly modify the viscosity of the composition prepared. In contrast, slight variations in the concentration of the thickener according to the prior art lead immediately to considerable modifications in the viscosity of the composition prepared.

The thickener in accordance with the invention thus makes it possible to obtain fluid emulsions, such as a milk, in a reproducible manner on an industrial scale, this not being the case for the thickener of the prior art.

EXAMPLE 5

The skin tolerance of the thickeners of Examples 1 and 3 was tested. The non-volatile oil constituting the thickener, introduced after copolymerization, is of variable nature.

The weight ratios between the isoparaffin and the non-volatile oil, which constitute the thickener, were also varied.

The tests were performed using an aqueous solution comprising (% by weight):

| | |
|---|---|
| thickner | 5.0% |
| water | 95% |

The results obtained are featured in the table below.

| Test | Non-volatile oil | Molecular weight of the non-volatile oil | Tolerance (%) as a function of the iso-paraffin/non-volatile oil weight ratio | | |
|---|---|---|---|---|---|
| | | | 47/53 | 67/33 | 100/0 |
| 1 | primol 352[(1)] | 470 | 100 | 60 | 15 |
| 2 | isostearyl isostearate | 536 | 85 | | |

[(1)]Thickened liquid paraffin marketed by the company Esso.

The skin tolerance was determined according to the so-called epicutaneous test under occlusion (patch test) in man.

Small aluminium cups 8 mm in diameter and 20 microliters in capacity were used, each cup allowing a surface area of 50 mm² to be covered. They are mounted in pairs on an adhesive tape.

The aqueous solution impregnates discs of blotting paper which are specially adapted to the cup/adhesive system. The system is applied to the skin (left sub-capular region) of the individuals. Fourteen volunteers, with an average age of 29, served as test individuals.

By way of reference, a 2% solution of sodium lauryl sulphate, as well as distilled water serving as a control, were also applied in the same manner to each individual but to a different area of skin.

24 hours after the application, the cups are removed from the areas on which they have been applied.

The results are read 30 minutes and then 24 hours after installation.

In order to examine whether or not the products applied are tolerated, the appearance of the following phenomena was considered:

erythema,
oedema,
blisters,
dry skin,
rough skin,
reflex excitability of the skin.

The percentage of skin tolerance expressed in the above table corresponds to the number of individuals who exhibited none of the phenomena mentioned above, relative to the total number of individuals, after the reading taken at 24 hours.

EXAMPLE 6

In order to assess the stability of the viscosity imparted by the thickener according to the invention, a dispersion of the thickener according to Example 1 in water was prepared, such that the viscosity obtained is 80 Pa s (Brookfield LVT4, 6 revolutions/minute).

By way of comparison, an aqueous dispersion thickened to 80 Pa s was prepared using the comparative thickener defined in Example 3.

0.1% by weight of a salt was then introduced into each of the thickened aqueous dispersions. This salt is either sodium chloride or magnesium chloride ($MgCl_2$).

The aqueous dispersion thickened with the thickener in accordance with the invention, in which sodium chloride is added, thus has its viscosity reduced to 57 Pa s with NaCl and to 61 Pa s with $MgCl_2$. The aqueous dispersion thickened with the comparative thickener has its viscosity fall to 13 Pa s with sodium chloride and to 16 Pa s with magnesium chloride.

EXAMPLE 7

A make-up-removing milk is prepared by mixing (% by weight):

| | |
|---|---|
| montanov 94[(7)]: | 3.0% |
| primol 352: | 8.0% |
| HAD[(8)]: | 2.0% |
| thickener of Example 1: | 0.8% |
| water qs | 100% |

[(7)]nonionic surfactant marketed by the company Seppic
[(8)]sweet almond oil marketed by the company Bertin.

A preserving agent and a fragrance were added to this mixture.

The viscosity of this composition is 15 Pa s and its pH is 7 (after adjustment); it is stable for 1 month at 50° C. and for 3 months at 40° C.

EXAMPLE 8

A body milk is prepared by cold-mixing (% by weight):

| | |
|---|---|
| lanol 99[9]: | 10.0% |
| thickener of Example 1: | 1.4% |
| micropearl M100[10]: | 0.2% |
| water qs | 100% |

[9]isononyl isononanoate marketed by the company Seppic
[10]polymethyl methacrylate marketed by the company Seppic A preserving agent and a fragrance are added to this mixture.

The viscosity of this composition is 12 Pa s and its pH is 6 (after adjustment); it is stable for 2 weeks at 50° C. and for 3 months at 40° C.

EXAMPLE 9

A body milk is prepared by mixing (% by weight):

| | |
|---|---|
| montanov 94: | 3.5% |
| lanol 37T[11]: | 8.0% |
| benzophenone: | 2.0% |
| dimethicone 350 cPs: | 0.05% |
| solagum L[12]: | 0.05% |
| thickener of Example 1: | 1.5% |
| water qs | 100% |

[11]glyceryl triheptanoate marketed by the company Seppic
[12]carrageenan marketed by the company Seppic A preserving agent and a fragrance are added to this mixture.

The viscosity of this composition is 18 Pa s and its pH is 6 (after adjustment); it is stable for 1 month at 50C and for 3 months at 40° C.

EXAMPLE 10

An emulsion which is fluid at alkaline pH is prepared by cold-mixing (% by weight):

| | |
|---|---|
| marcol 82[13]: | 5.0% |
| thickener of Example 1: | 1.5% |
| NaOH: | 10% |
| water qs | 100% |

[13]liquid paraffin marketed by the company Esso.

The viscosity of this composition is 10 Pa s and its pH is 12 (after adjustment); it is stable for 2 weeks at 50° C. and for 3 months at 40° C.

EXAMPLE 11

A fluid foundation is prepared by mixing (% by weight):

| | |
|---|---|
| simulsol 165[14]: | 5.0% |
| lanol 99: | 5.0% |
| lanol 84D[15]: | 8.0% |
| thickener of Example 1: | 1.2% |
| inorganic fillers and pigments: | 10.0% |
| water qs | 100% |

[14]self-emulsifiable glyceryl stearate marketed by the company Seppic
[15]dioctyl malate marketed by the company Seppic.

A preserving agent and a fragrance are added to this mixture.

The viscosity of this composition is 20 Pa s and its pH is 6 (after adjustment); it is stable for 1 month at 50° C. and for 3 months at 40° C.

EXAMPLE 12

A sun milk is prepared by mixing (% by weight):

| | |
|---|---|
| montanov 94: | 3.5% |
| lanol 37T | 10.0% |
| parsol NOX[16]: | 5.0% |
| eusolex 4360[17]: | 2.0% |
| thickener of Example 1: | 1.8% |
| water qs | 100% |

[16]sunscreen marketed by the company Givaudan
[17]sunscreen marketed by the company Merck.

A preserving agent and a fragrance are added to this mixture.

The viscosity of this composition is 18 Pa s and its pH is 7 (after adjustment); it is stable for 1 month at 50° C. and for 3 months at 40° C.

EXAMPLE 13

A gel to be applied around the eyes is prepared by mixing (% by weight)

| | |
|---|---|
| thickener of Example 1: | 2.0% |
| sodium pyrrolidonecarboxylate: | 0.2% |
| cyclomethicone[18]: | 2.0% |
| water qs | 100% |

[18]Dow Corning 245 fluid marketed by the company Dow Corning.

A preserving agent and a fragrance are added to this mixture.

The viscosity of this composition is 15 Pa s and its pH is 6 (after adjustment); it is stable for 2 weeks at 50° C. and for 3 months at 40° C.

What is claimed is:

1. In a thickener for a composition for topical application, consisting essentially of a water-in-oil reverse emulsion of a copolymer of acrylic acid and acrylamide, wherein the copolymer contains a polyfunctional monomer in an amount between 0.1 and 2 milliequivalents per mol of the other monomers, and wherein the copolymer is in solution in the aqueous phase constituting the said emulsion, the oil phase of this emulsion consists of a mixture of at least one volatile oil and at least one non-volatile oil, the weight ratio between the volatile oil and the non-volatile oil is between 70/30 and 30/70, the oil phase represents from 10 to 60% by weight of the whole, water represents from 30 to 70% by weight of the whole, the copolymer represents from 10 to 30% by weight of the whole and surfactant represents from 5 to 20% by weight of the whole, and wherein the volatile oil is a volatile isoparaffin and the non-volatile oil is a paraffin or isostearyl isostearate.

2. Composition according to claim 1, wherein the thickener also comprises at last one surfactant whose HLB is at least 8.

3. Composition according to claim 2, wherein said HLB is at least 10.

4. Composition according to claim 1, wherein the emulsion is a milk or a liquid gel.

* * * * *